US007428848B2

(12) United States Patent
Pant et al.

(10) Patent No.: US 7,428,848 B2
(45) Date of Patent: Sep. 30, 2008

(54) ELECTROSTATIC SAMPLER AND METHOD

(75) Inventors: Kapil Pant, Huntsville, AL (US); Guiren Wang, Huntsville, AL (US); Jianjun Feng, Huntsville, AL (US); Shankar Sundaram, Madison, AL (US)

(73) Assignee: CFD Research Corporation, Huntsville, AL (US)

( * ) Notice: Subject to any disclaimer, the term of this patent is extended or adjusted under 35 U.S.C. 154(b) by 277 days.

(21) Appl. No.: 11/199,754

(22) Filed: Aug. 9, 2005

(65) Prior Publication Data

US 2007/0034025 A1 Feb. 15, 2007

(51) Int. Cl.
*G01N 1/24* (2006.01)

(52) U.S. Cl. .................. 73/863.21; 73/28.02; 73/28.04; 73/864.33; 73/864.34; 250/288; 435/30; 435/309.1

(58) Field of Classification Search .............. 73/864.33, 73/864.34, 863.21, 28.04, 28.01, 28.02, 31.02; 435/30, 309.1; 250/283–284, 288–289
See application file for complete search history.

(56) References Cited

U.S. PATENT DOCUMENTS 3,478,205 A * 11/1969 Sporek ...................... 73/23.35
3,906,237 A * 9/1975 Pittaway ..................... 250/489
4,266,196 A * 5/1981 Kawazoe et al. ....... 313/231.71
4,284,496 A * 8/1981 Newton ...................... 209/3.3
4,410,854 A * 10/1983 Kroneisen et al. ........... 324/468
4,866,278 A * 9/1989 Lovelock ................ 250/283 X
6,005,245 A * 12/1999 Sakairi et al. ........... 250/288 X
7,164,122 B2 * 1/2007 Fuhrer et al. ................ 250/287
7,243,560 B2 * 7/2007 Coyle et al. ............ 73/28.02 X
2004/0083790 A1 * 5/2004 Carlson et al. ............. 73/28.02

FOREIGN PATENT DOCUMENTS

FR 2309973 A * 12/1976
SU 1295337 A * 3/1987

* cited by examiner

*Primary Examiner*—Thomas P Noland
(74) *Attorney, Agent, or Firm*—Tomas Friend, LLC

(57) ABSTRACT

The present invention is an electrostatic collector for low cost, high throughput, high efficiency sampling and concentration of bioaerosols. The device is small enough to be portable and can be contained within or placed on the wall of a typical office or hospital building. The collector comprises one or more collector modules, each having an ionizing electrode, a conical outer electrode, a wet collection electrode, and a liquid collection system. Airflow through a collector module may be partially blocked to enhance the collection of smaller particles and the collection electrode may comprise multiple, programmable electrodes to focus particle deposition onto a smaller area. Particles are collected into a small volume of liquid to facilitate subsequent analysis by an attached analyzer or at a remote site.

20 Claims, 10 Drawing Sheets

SIDE VIEW (B)

END VIEW
(A)

SIDE VIEW
(B)

Arrayed Arrangement of Anti-symmetrically Blocked ECMs (not to scale)

Figure 10

A  B

ELECTROSTATIC SAMPLER AND METHOD

STATEMENT REGARDING FEDERALLY SPONSORED RESEARCH/DEVELOPMENT

Statement of Government Rights

The U.S. Government may have certain rights in this invention pursuant to HSARPA SBIR Contract NBCHC040110 awarded by the Department of Homeland Security.

CROSS-REFERENCE TO RELATED APPLICATIONS

Not Applicable

INCORPORATED-BY-REFERENCE OF MATERIALS ON A CD

Not Applicable

BACKGROUND OF THE INVENTION

1. Field of the Invention

This invention relates generally to electrostatic samplers and methods used to collect aerosolized particulates. The particulates are collected on a dry collection surface or in a buffer solution or other liquid to facilitate subsequent processing and analysis. In particular, this invention provides a miniaturized electrostatic sampler designed for high efficiency and low energy (cost) collection of airborne particulates. The airflow through the sampler, electric fields, and collector geometry were obtained using physics-based computational optimization methods to maximize capture efficiency and selectivity for a target particle size while minimizing power consumption and device footprint.

2. Description of Related Art

The detection and analysis of aerosolized biological agents such as bacteria, bacterial, mold, and fungal spores, and viruses is desirable in a wide variety of settings including civilian environs such as hospitals, office buildings, and sports arenas, as well as military environments such as the battlefield, observation posts, and military housing. The ability to detect airborne particles such as bacteria and bacterial spores is critical to areas where accidental or deliberate release of harmful biological agents is suspected and can greatly help risk assessment and management, decontamination/neutralization and therapeutic efforts. Rapid detection of airborne pathogens can control the spread of bacterial infections in hospitals, schools, and animal facilities, for example.

In recent years, increasing concern has been expressed over the development of fast, accurate and robust countermeasures against the emergent threat of bioterrorism. A comprehensive review of biodetection technologies is provided in the following reference: NATIONAL RESEARCH COUNCIL OF THE NATIONAL ACADEMIES (2005) "Sensor Systems for Biological Agent Attacks: Protecting Buildings and Military Bases" Committee of Materials and Manufacturing Processes for Advanced Sensors, Board on Manufacturing and Engineering Design, Division on Engineering and Physical Sciences, The National Academies Press, Washington, D.C. Typically, the process of biodetection can be broadly sub-divided into the following steps: (1) sampling, where the airborne particles are captured into a suitable solid, liquid or gaseous matrix, (2) sample preparation, where the aforementioned matrix is processed to render the target entities in a format aligned with the downstream detector, and (3) sensing, where the target moieties in the sample are identified.

Reviews of bioaerosol sampling strategies are provided in the following references: National Institute of Justice (NIJ) Guide 101-00 (2001) "An Introduction to Biological Agent Detection Equipment for Emergency First Responders" US Department of Justice, Washington, D.C.; and HENNINGSON et al. (1994) "Evaluation of Microbiological Aerosol Samplers: A Review" Journal of Aerosol Science 25(8):1459-1492. Existing bioagent sampling technologies are largely based on (a) interception (such as filters), (b) inertial separation mechanisms (such as impingers, impactors, cyclones and centrifuges) or (c) electrostatic principles. Interception based aerosol samplers are a primarily intended for air purification and suffer from high costs of maintenance, difficulties in interfacing with analysis modalities and pre-determined cut-off size for sampling. Inertial separation mechanisms suffer from the disadvantages of high cost of operation, high power consumption, low collection efficiencies of viable microorganisms, and high cost of manufacturing/machining. Electrostatic precipitators, as opposed to samplers/collectors, are commonly used as air purifiers designed to filter air and not to capture airborne particulates on a substrate or matrix for analysis. Existing electrostatic samplers are too large for portable applications and use voltages that kill or damage many organisms, thus preventing or complicating organism detection and identification.

Recently, the use of electrostatic samplers for collection of airborne microorganisms was demonstrated by the following references: MAINELIS et al. (2002) "Design and Collection Efficiency of a New Electrostatic Precipitator for Bioaerosol Collection" *Aerosol Science and Technology* 36:1073-1085; and MAINELIS et al. (2002) "Collection of Airborne Microorganisms by a New Electrostatic Precipitator, *Journal of Aerosol Science* 33:1417-1432, which are incorporated by reference in their entirety. A simple design comprising a parallel plate electrode configuration was used for developing the proof-of-concept in these studies. Physical collection efficiencies of >90% and biological collection efficiencies of >70% were demonstrated for air flow rates up to 8 L/min. Electrostatic samplers use an externally applied voltage to charge particulates in the air and deposit them on a collection surface. The collection surface can be an electrode with a dry surface or an electrode covered with a stationary or moving liquid. Electrostatic collectors (samplers) that deposit particles in a liquid medium can be used to concentrate samples from the air and deliver them to fluid-based biological assay modules such as microfluidic chips for analysis. This format is particularly useful for detecting or identifying biological agents such as bacteria, viruses, and bacterial, mold, and fungal spores, for example.

U.S. Patent Publication 2004/0083790 (CARLSON et al.) describes a portable liquid collection electrostatic precipitator. The device comprises: a hollow, vertical, tubular collection electrode; a ground plate adjacent to the collection electrode; a reservoir for a liquid, a pump for pumping the liquid, and an ionization section to ionize analytes in the air. Particles in the air are ionized, attracted to the collection electrode, and precipitated in the liquid. The device described by CARLSON et al. uses a high voltage collection electrode of 6,000-8,000 volts to attract charged particles, an airflow rate of 300 L/min, and can be powered by a 12-volt automobile battery. High voltages such as those applied to the Carlson et al. collection electrode can kill many organisms and thereby prevent or make more difficult their detection and/or identification. In addition, the high voltage applied at the collection electrode, which is normally bathed in aqueous liquid, poses a significant safety hazard. The CARLSON et al. sampler does not disclose the collection of small diameter particles with high efficiencies or designs capable of miniaturization while maintaining high collection efficiencies.

There remains an unmet need in the art for a miniaturized, portable electrostatic air sampler that can collect particles, including viable airborne viruses and bacterial spores, with high efficiency.

The present inventors have applied physics-based computational fluid dynamics (CFD) analysis to design novel, miniaturized electrostatic samplers that occupy less space, consume less power, capture particles with higher efficiency, and have greater operational flexibility than existing electrostatic samplers/collectors. Several innovative concepts for high throughput sampling were identified and evaluated using coupled airflow, particle transport and electric field simulations. The optimized samplers have predicted collection efficiencies of >90% at <5,000V and 60 L/min, even for 1 μm particles. Clustering of collectors in an electrostatic sampler array can easily achieve airflow rates of 300-1000 L/min and higher. A high voltage outer electrode allows the use of a grounded collection electrode to maintain the viability of collected cells and spores. The outer and/or collection electrode may be segmented to form programmable electrode array(s) to enhance efficiency and to reduce the area onto which particles are deposited. Testing of a prototype electrostatic sampler design has verified the performance predicted by CFD simulations.

BRIEF SUMMARY OF THE INVENTION

The present invention provides various embodiments of a miniaturized electrostatic air sampler comprising at least one electrostatic collector module (ECM) for depositing airborne particulates such as bioagents, dust particles, and aerosolized chemicals, onto a dry substrate or into a small volume of liquid collection medium. The electrostatic air sampler operates with high particle capture efficiencies using outer electrode voltages of less than 5,000 volts, more preferably, less than 2000 volts, and most preferably, less than 1000 volts, and consumes less than 100 Watts for the device and less than 10 Watts for each ECM. The miniaturized sampler is capable of collecting viable, aerosolized organisms from the air or other gasses to facilitate the analysis, identification, and quantification of the organisms. The miniaturized sampler can operate on battery power for portablility and maintains at least 90% collection efficiency for particles having diameters of 1-10 μm while operating at air flow rates of between about 60 L/min to 1000 L/min. The miniaturized electrostatic sampler may be coupled to at least one analyzer for detecting or identifying at least one specific bioagent, and may be equipped to transmit information related to the presence, absence, and/or concentration of one or more bioagents in the collected sample and/or the sampled air to a local or remote location.

Important findings during the design of the present miniaturized air sampler include: the superior performance of tapered, especially conically shaped ionizing electrodes, the ability to enhance small particle capture by selectively blocking airflow through portions of the ECM, and the ability to selectively focus particle deposition onto regions of the collecting electrode by using a variable voltage outer electrode array.

BRIEF DESCRIPTION OF THE SEVERAL VIEWS OF THE DRAWINGS

FIG. 1 depicts a cut away view one prototype electrostatic sampler comprising one ECM with a wet collection electrode.

FIG. 2 illustrates one embodiment of the electrostatic sampler used for biohazard detection.

FIG. 3A depicts a first embodiment of an ECM.

FIG. 3B shows the simulated size-based collection efficiency for the ECM embodiment shown in FIG. 3A.

FIG. 4A shows a second embodiment of an ECM.

FIG. 4B shows the simulated size-based collection efficiency for the ECM embodiment shown in FIG. 4A.

FIG. 5 compares the simulated size-based collection efficiencies of first and second embodiments of an ECM for small particles.

FIG. 6A-D illustrate the effects of blocking flow on particle capture.

FIG. 7A-D illustrate the effects of blocking flow on particle trajectories.

FIGS. 8A and B show simulated overall and effective collection efficiencies

FIGS. 9A and B an arrayed arrangement of partially blocked ECMs

FIGS. 10A and B illustrate one embodiment in which performance improvements can be achieved by applying a programmed variable voltage to the outer electrode instead of a constant voltage.

DETAILED DESCRIPTION OF THE INVENTION

FIG. 1 shows one prototype electrostatic sampler comprising one ECM 10 with a wet collection electrode 2. A housing 11 contains ECM 10, liquid inlet 6, liquid outlet 7, and reservoir 8. The position of the ionization electrode 5 relative to the ECM 10 is indicated. During wet electrode operation, the sampler is vertical and a pump (not shown) pumps liquid into liquid inlet 6 and into the hollow cavity 9 of the collection electrode 2. The hollow cavity 9 fills and liquid flows over the lip 12, down the sides of the collection electrode 2, and into the reservoir 8. Fluid from the reservoir may be recirculated into liquid inlet 6 or transferred, for example, to an analytical device. Air enters the ECM through air inlet 3, travels through the ECM between the outer electrode 1 and collection electrode 2, and exits through air outlet 4. Airborne particles are charged by the ionization electrode 5 and are driven into the liquid covering collection electrode 2 by a high voltage applied to outer electrode 1, which has the same charge as that imposed on the particles. The collection electrode 2 is grounded and has a charge opposite that of the particles and outer electrode.

The ionization electrode and outer electrode are energized by a high voltage potential provided by an electrical power supply. The power supply may be, for example, standard 110 or 220 AC or one or more DC batteries for portable operation. High voltages may be generated by well known means such as transformers or voltage amplifiers.

For some applications, it may be advantageous to include a charge neutralization section upstream of the location of the ionization electrode 5. In most cases, an electrostatic sampler will operate using an ionizing electrode that imparts a negative charge on airborne particles combined with a positively charged collection electrode. This is done because most biological particles carry or are easily caused to carry a negative charge. Some naturally occurring or manufactured biological aerosols carry a positive charge and do not maintain negative charges very well. Pretreatment with a charge neutralizer removes positive charges from these particles and makes it easier to imparting a negative charge on them. This tandem arrangement of charge neutralizer followed by ionization electrode can be used, for example, to sample for particles that naturally carry negative charges and those that carry positive charges. To specifically sample for particles carrying a positive charge, one would use an ionization electrode that imparts a positive charge on particles in combination with a negatively charged collection electrode.

Figure 1:
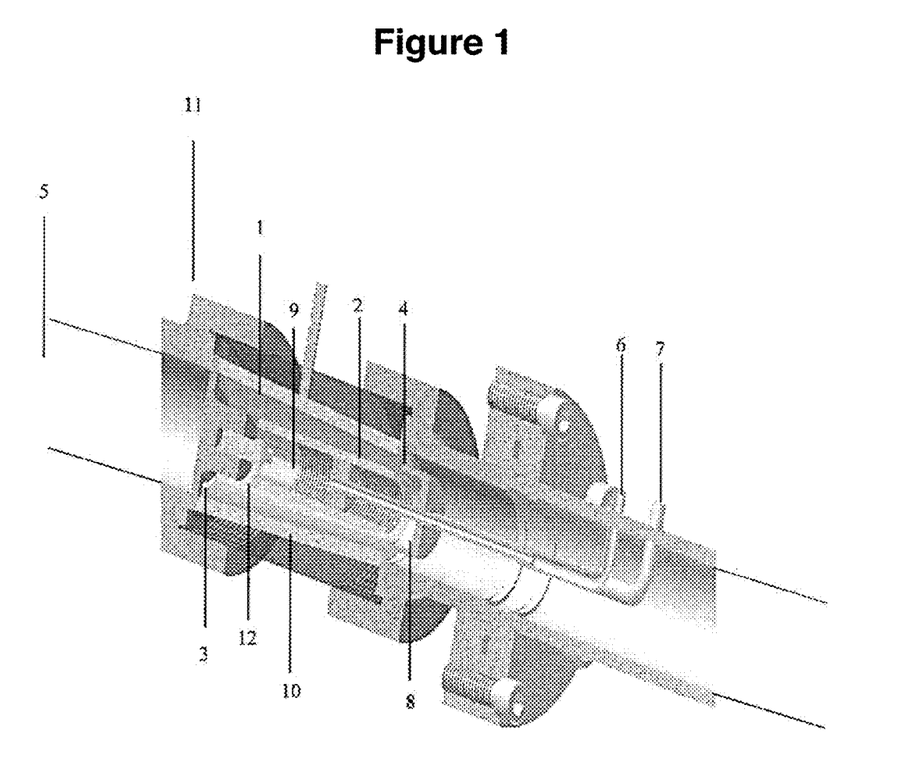
Figure 2:
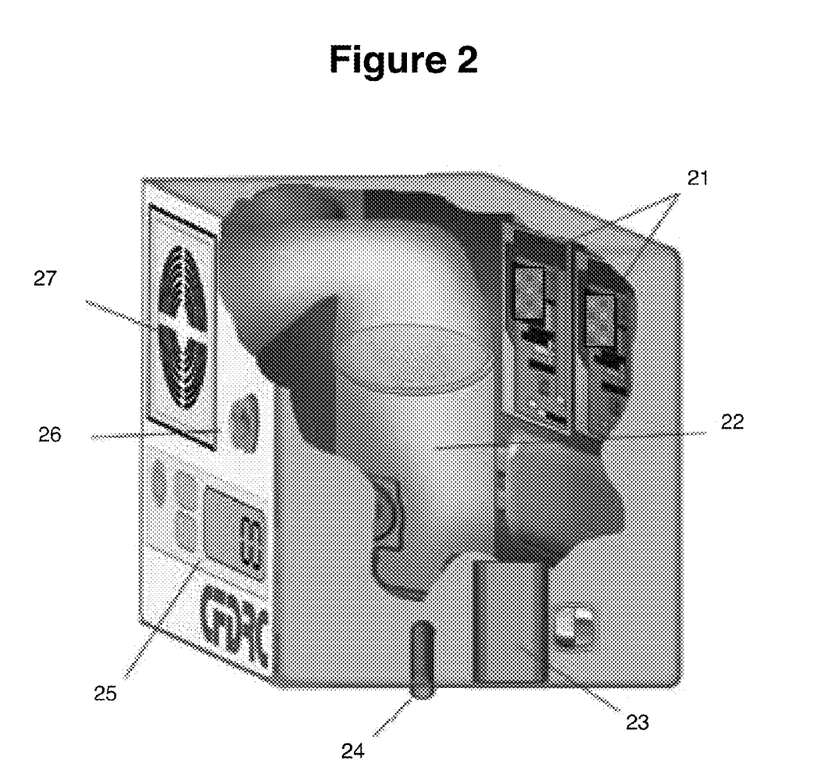

FIG. 2 illustrates one embodiment of the electrostatic sampler used for biohazard detection. Shown are: electronics for power supply modulation 21, a modular electrostatic sampling unit 22 comprising more than one ECM, a detachable well for collected sample analysis 23, an outlet to a detection platform 24, control panel and digital readout display 25, an indicator alarm 26, and active air intake 27.

Figure 3:
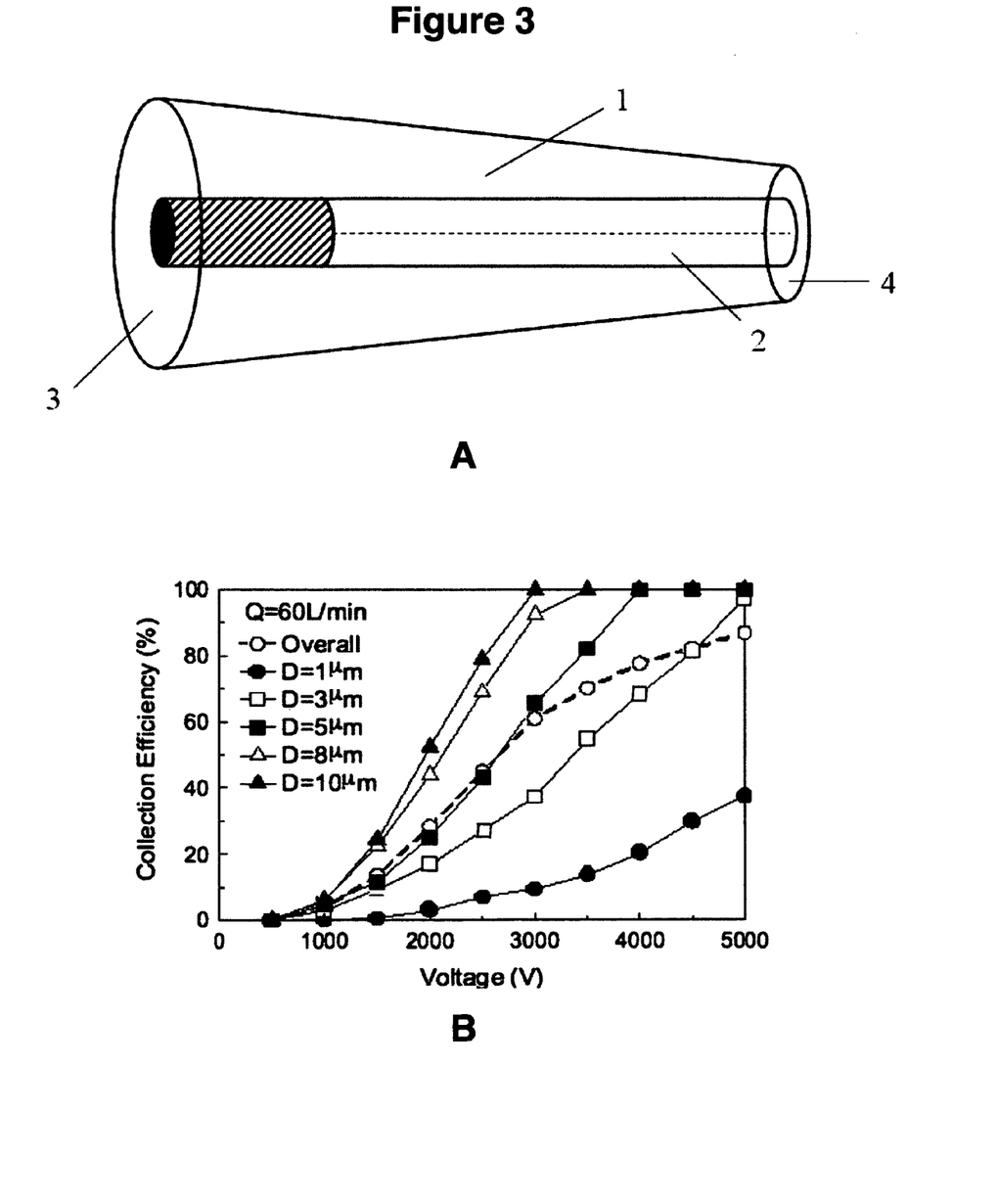

FIG. 3A shows one embodiment of an ECM. The ECM comprises a conical, high voltage outer electrode 1, forming at least a part of the outer wall of airflow channel 5 and a cylindrical, grounded, collecting electrode 2. This particular embodiment shows the collecting electrode 2 having a lighter shading than the upstream segment of the interior surface of the airflow chamber. In other embodiments, the collection electrode may comprise more or less of the interior surface of the airflow chamber. An ionization electrode upstream of and near the air inlet 3 is not shown. Air enters the ECM through inlet 3 and exits through outlet 4 of lesser diameter than inlet 3. Airflow can be forced, for example, by a fan, blower, or pressure differential or it can be passive and depend on the prevailing air currents around the sampler.

The shape of the outer electrode is most preferably a continuously narrowing conical shape but may have any continuously tapering shape from the air inlet to the air outlet. The outer electrode may also have a conical shape combined with cylindrical extensions at either end. The outer electrode may comprise a single, continuous segment of conducting material or a segmented series of electrodes that are insulated from one another to facilitate the programmed application of voltages to independent electrode segments. The outer electrode may comprise a portion of or all of the outer surface of the airflow channel 5. The outer electrode may be made of a conducting metal such as copper, gold, or platinum, a conducting polymer, or a nonconducting material coated with a conducing layer.

Ionized particles are directed toward the collection electrode by an electric field generated at the outer electrode. The collection electrode may be a solid or hollow cylinder of conducting material or nonconducting material coated with a conducting layer. Particles deposited on the collection electrode may be recovered in a variety of ways. It the collection electrode is dry, deposited particles may be transferred to a material used to wipe the electrode or transferred into a container by scraping, blowing, or other means. If the electrode is wet, liquid may be dispensed over the surface of the electrode in a continuous or discontinuous fashion. Liquid may be recirculated over the electrode and periodically transported to an analysis unit or continuously or discontinuously flow over the collection electrode and into an analysis unit.

For wet electrode operation, the ECM further comprises a pump and liquid reservoir, which provide a periodic or constant film of collection liquid flowing over the surface of the grounded collection electrode. During wet electrode operation, the electrode should be evenly covered by a thin film of liquid, which may be water, an aqueous buffer, an organic solvent, an oil, or any other suitable fluid that can form a thin, flowing layer on the collection electrode. The collection electrode may be coated with a material to facilitate even spreading of the liquid and/or the liquid may comprise a surfactant to facilitate even spreading. The wet collection electrode is normally a vertical hollow cylinder that fills at the bottom with fluid from a pump, with liquid running over the top lip of the cylinder, down the outer walls, and into a reservoir that feeds back into the pump. The top of the collection electrode cylinder may be partially covered but may not interfere with fluid flow over the lip to the outside walls. The collection electrode and ECM need not be vertical during wet operation in microgravity conditions or if a continuous, thin layer of liquid can be maintained on the collection electrode and the liquid can be returned to the reservoir.

CFD simulations of airflow through the ECM show that, compared to a cylindrical shape, the conical shape of the outer electrode increases flow stability, particularly when airflow around the air inlet 3 is chaotic, as would be the case for a sampler used outdoors with variable winds. The conical design also directs airflow toward the collection electrode, increasing collection efficiency. The angle of the conical electrode is preferably between $1°$ and $4°$ to optimize airflow stability without decreasing efficiency caused by increased air velocity at the collection electrode. The ECM can be modified to optimize the collection efficiency for certain particle sizes and densities. The air inlet and outlet may be partially blocked to enhance the efficiency for small particle collection, for example. The outer electrode may also be segmented to allow variable voltage application along the outer electrode to direct selected particles toward specified areas of the collection electrode.

FIG. 3B shows the size-based, CFD simulated collection efficiencies of the ECM shown in FIG. 3A. Larger particles are collected with higher efficiency at lower outer electrode voltages, while smaller particles are collected with higher efficiency at higher voltages. The collection efficiencies predicted by CFD simulations have been experimentally validated using an actual corresponding prototype ECM with airborne particulates including polymer beads and sub-micrometer sized salt particles.

Figure 4:
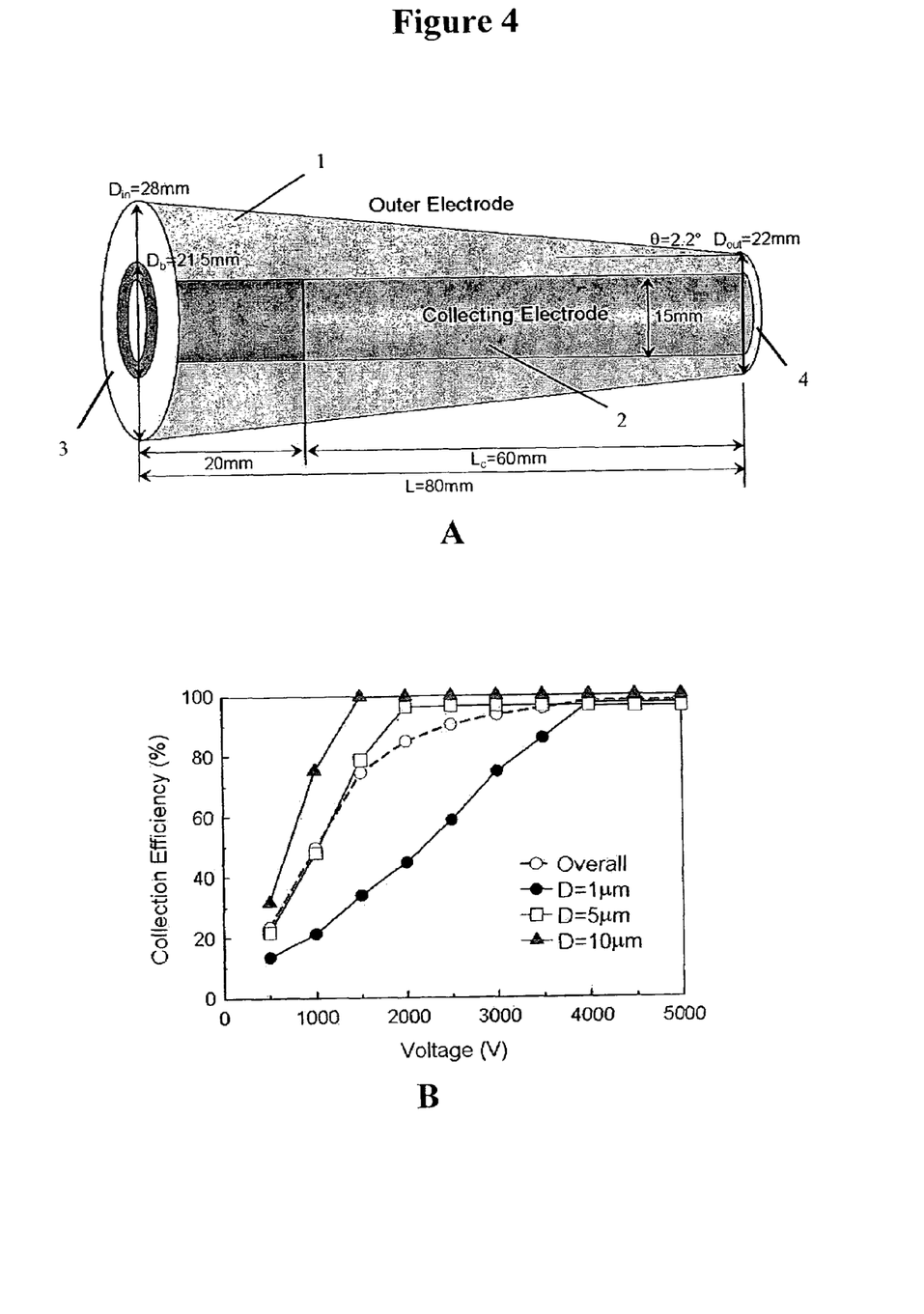
Figure 5:
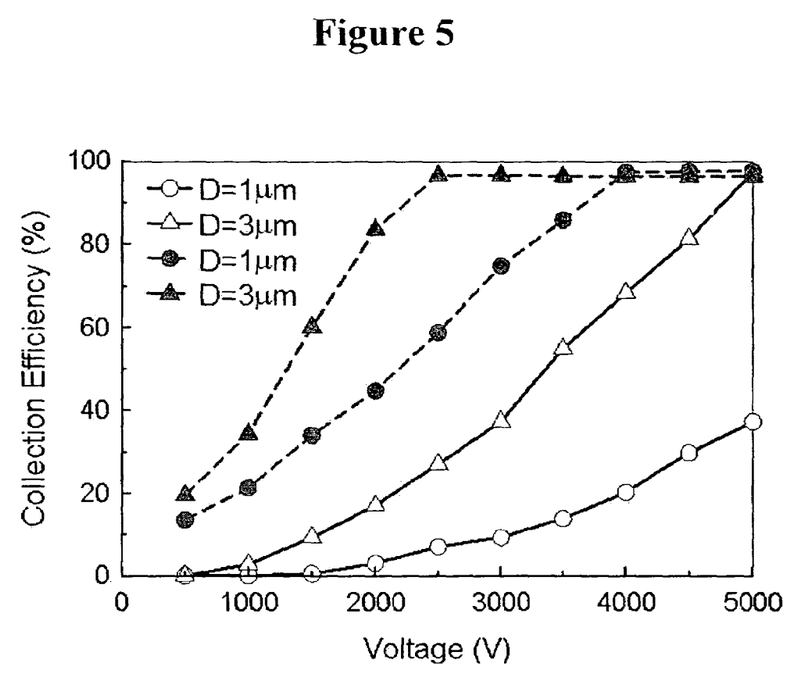
Figure 6:
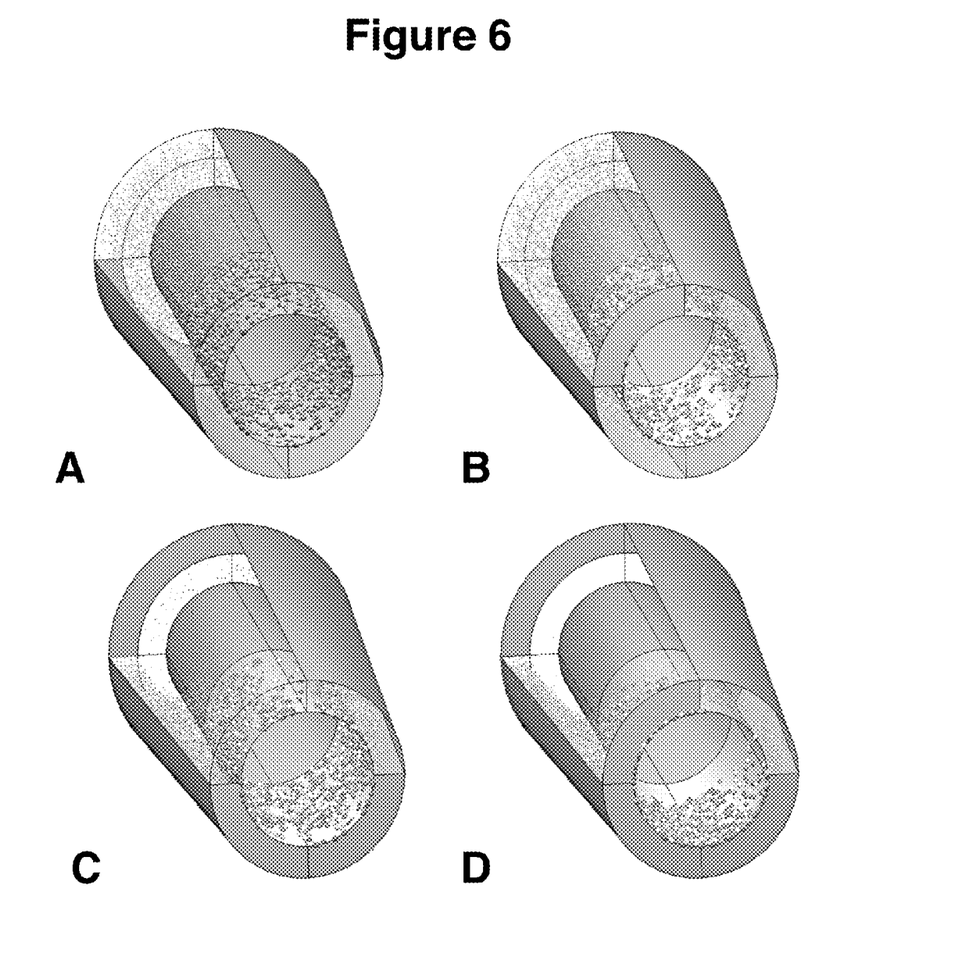
Figure 7:
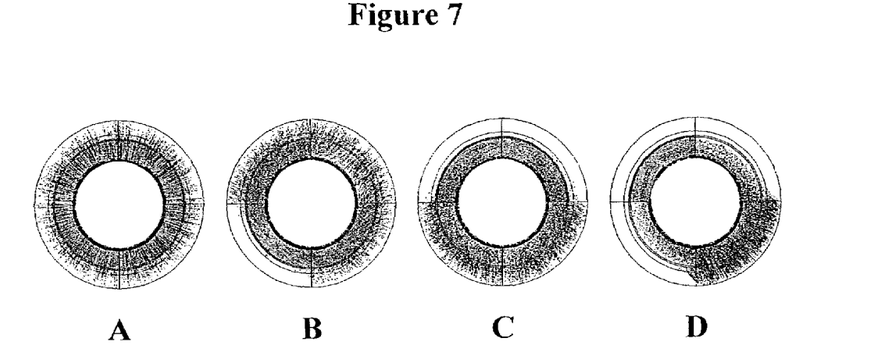
Figure 8:
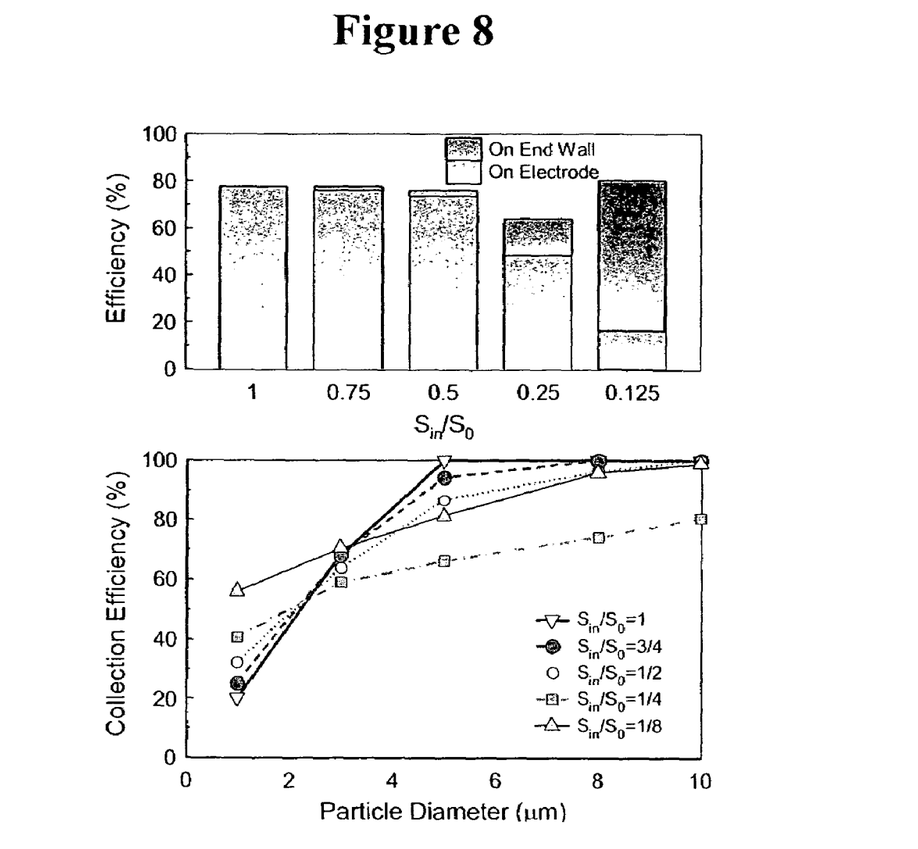
Figure 9:
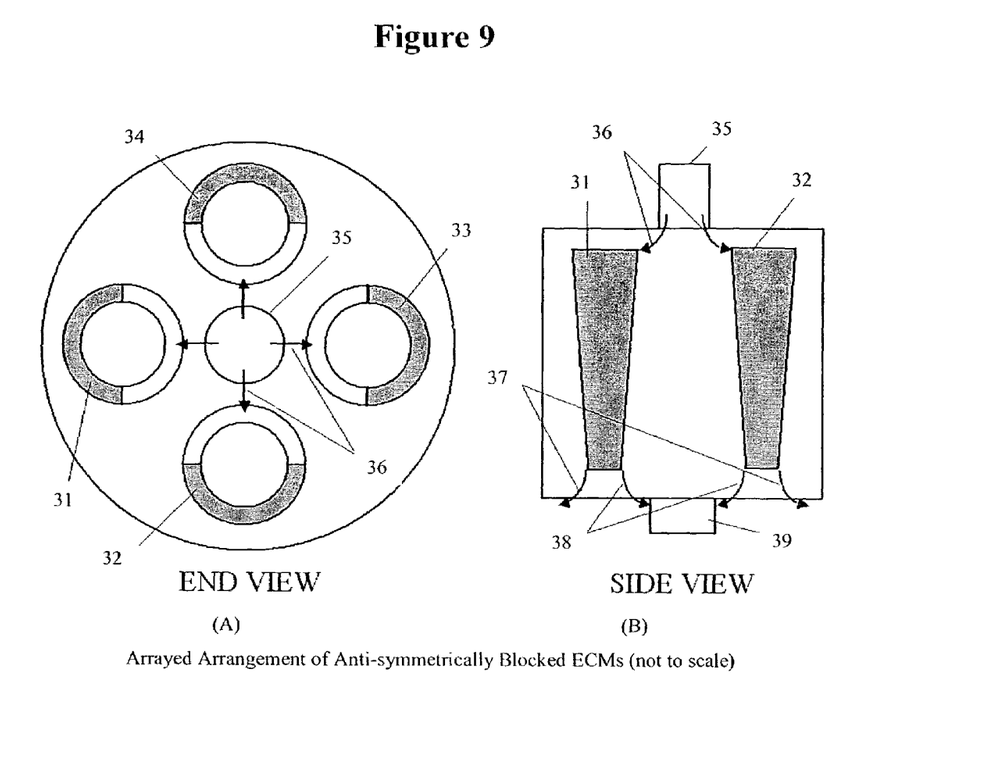
Figure 10:
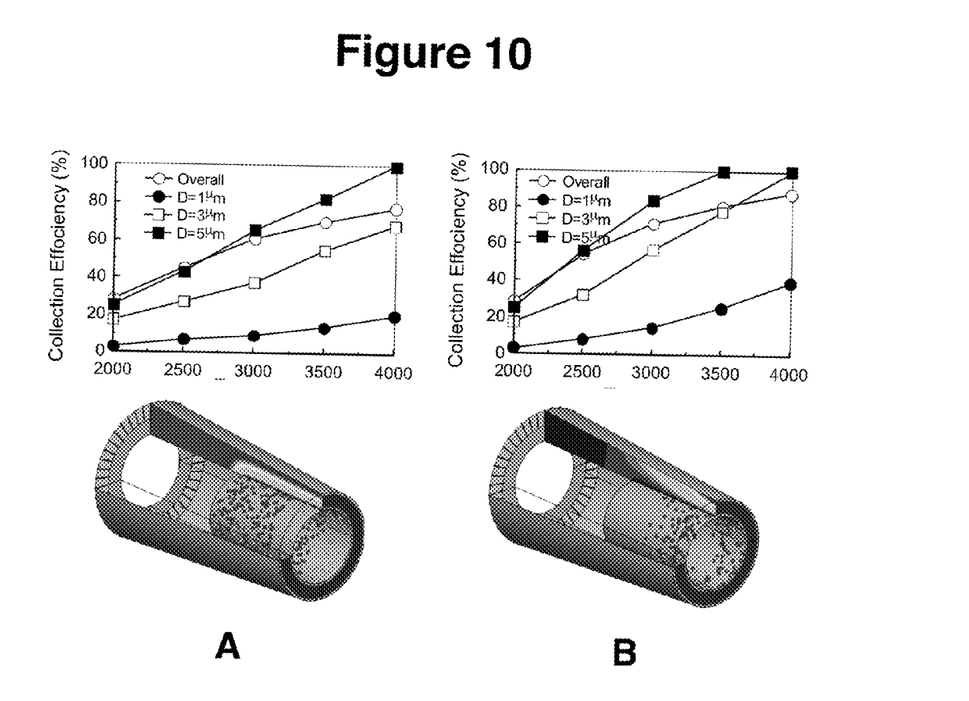

FIG. 4A shows a second embodiment of an ECM that was redesigned to optimize small particle collection using CFD simulations. The collecting electrode 2 of this embodiment is shown in a lighter shade than the upstream portion of the inner wall of the airflow chamber. The size-based CFD simulated collection efficiencies for small particles of the second embodiment ECM are shown in FIG. 4B. The collection efficiencies for smaller particles are improved over those for the ECM shown in FIG. 3A. FIG. 5 compares the small particle collection efficiencies of the ECMs shown in FIG. 3A (open circles and triangles) and FIG. 4A (shaded circles and triangles). The collection efficiencies for 1 μm and 3 μm particles are virtually 100% below applied outer electrode potentials of 5,000 volts for the second ECM. The CFD simulations have been supported by the results of experiments using two corresponding prototype ECMs with airborne particulates including polymer beads and sub-micrometer sized salt particles.

In some embodiments of the invention, it may be desirable to alter the pattern of airflow through one or more ECMs. For example, one may place vanes that are slanted or otherwise shaped to induce tangential, spiral, laminar airflow in the ECM. Such flow increases particle residence time in the ECM and prolonging the time during which charged particles are exposed to the electric field driving them toward the collection electrode. In some cases it may be advantageous to partially block the air inlet and outlet of one or more ECMs. For example, for manifold samplers that comprise multiple ECMs in close proximity, it may be advantageous to partially block inlet and outlet ends to prevent the separation of air and liquid sample streams. The blocked areas at inlet and outlet ends would be maintained anti-symmetric to the centerline to avoid "short-circuiting" of particles in the chamber. Coupled multiphysics simulations were carried out to evaluate a modular design comprising 5 ECMs arranged in parallel and in a pentagonal arrangement. FIG. 6A-D shows sample simulation results for both 3D and projected particle trajectories. The effective inlet area is shown by dark gray for 0, 25%, 50% and 75% blockage.

Partially blocking the air inlet and outlet introduces cross-flow patterns in the airflow chamber and enhances the collection of smaller particles. FIG. 6A-D shows the simulated distributions of captured particles on the collection electrode for different levels of airflow blockage. Particle capture is not symmetrically distributed on the collection electrode because of cross-flow. More particles are captured on the "windward" side of the inner electrode than the "leeward" side. Partially blocked ECMs may be used to enhance small particle collection while reducing large particle collection or to focus collection on a particular area of the collection electrode. Reducing the area of deposition in the collection electrode may, for example, allow the use of smaller volumes of liquid for particle collection or, in the case of dry collection electrodes, may allow a higher concentration of deposited particles for collection by other means.

FIG. 7A-D shows the particle trajectories for different levels of airflow blockage. The effective blockage at the inlet is shown in white for 0, 25%, 50% and 75% blockage. Since part of the outlet is blocked, higher particle velocity and cross-flows cause some particles to be lost at the exit. The simulated overall collection efficiencies are shown in FIG. 8. The overall collection efficiency contains particles captured on the inner electrode as well as those on the end wall. An increase in blockage (decreasing $S_{in}/S_0$) leads to an increase in the collection efficiency of small particles and a loss of larger particles at the outlet.

Partially blocked ECMs may also be useful when combining several ECMs into one sampler device. FIG. 9A-B show an array of four partially blocked ECMs 31, 32, 33 and 34 arranged in a circular fashion. Due to the annular path of the air stream, it is advantageous to employ partially blocked ECMs in arrayed configurations. The inlet airflow path 36 is shown in FIG. 9A-B along with air exit stream 37. Partial blocking of the proximal (inlet) and distal (outlet) ends of the ECM allows the realization of a simplified manifold such as a single manifold 35 located near the axis of a circular array of ECMs. For wet electrode collection, the simplification of airflow manifold design can be propagated to the distal end and harnessed for a centralized collection buffer manifold 39 fed by the liquid stream 38 from individual ECMs. One sampler device may have any number of identical or different ECMs combined in parallel and/or in series, depending on the desired application. For example, parallel configurations allow for increased airflow while ECMs in series may allow for sequential optimized sampling for different airborne species. Other examples of advantages provided by ECM arrays include simultaneous optimized sampling for different airborne particles and redundancy for internal controls and reduction of false positive and false negative results.

In another embodiment of the invention, it may be desirable to segment the outer, conical electrode so that the potential is applied in a programmed fashion as opposed to a constant, uniform potential. This leads to improved collection efficiency and a more focused collection of particles as shown in FIGS. 10A and B.

EXAMPLE

Two prototype electrostatic samplers representing two embodiments of the invention were fabricated and tested. The design and performance specifications based on experiments using airborne polystyrene beads are displayed in Table 1 for one of the samplers.

TABLE 1

Specifications for a One Embodiment of an Electrostatic Sampler

| Design Specifications | | Performance Specifications | |
|---|---|---|---|
| Electrode Shape | Conic | Air Flow Rate | 60 L/min |
| Chamber Length | 50-100 mm | Pressure Drop | <1" of water |
| Electrode Length | 25-50 mm | Collection Efficiency | >90% (1-10 μm) |
| Electrode Diameter | 15 mm | Liquid Collection Volume | 10 ml |
| Inlet Diameter | 28 mm | Applied Voltage | 2000-5000 V |
| Outlet Diameter | 22 mm | Size & Weight | 1 $ft^3$, ~2 lb |

It will be appreciated by those having ordinary skill in the art that the examples and preferred embodiments described herein are illustrative and that the invention may be modified and practiced a variety of ways without departing from the spirit or scope of the invention. Combinations of sampler, ECM, outer electrode, collection electrode, air inlet and air outlet dimensions, outer and collection electrode shapes, programmed application of voltages to segmented outer electrodes, and combinations of ECMs into samplers may be adapted for particular sampling needs without departing from the present invention.

What is claimed is:

1. An electrostatic air sampling device comprising:

an electrostatic collection module comprising:

an airflow chamber comprising an air passage having an air inlet and an air outlet;

a means of drawing air into the air inlet, through the airflow chamber, and out through the air outlet;

an ionization electrode located near the air inlet, the ionization electrode being capable of ionizing airborne particles;

a conical outer electrode forming at least a part of the outer wall of the airflow chamber and having a larger diameter toward the air inlet and a smaller diameter toward the air outlet;

a cylindrical, collection electrode, the exterior surface of which forms at least a part of the inner wall of the airflow chamber and upon which airborne particles are collected; and a power source operatively connected to the electrostatic collection module, said power source providing power to energize the ionization and outer electrodes.

2. The electrostatic air sampling device of claim 1, wherein the total length of the electrostatic collection module is less than 25 cm and the total width of the electrostatic collection module is less than 10 cm.

3. The electrostatic air sampling device of claim 1, wherein the air inlet and air outlet of the airflow chamber are partially blocked.

4. The electrostatic air sampling device of claim 1, wherein the air inlet of the airflow chamber comprises one or more vanes that cause tangential, spiral, laminar airflow in the airflow chamber.

5. The electrostatic air sampling device of claim 1, wherein the conical, outer electrode comprises a series of electrode segments.

6. The electrostatic air sampling device of claim 1, wherein the collection electrode is grounded.

7. The electrostatic air sampling device of claim 1, further comprising a transceiver operationally connected to the electrostatic air sampling device for:
controlling the operation of the device in response to received signals and sending information from the device to a remote location.

8. The electrostatic air sampling device of claim 1, wherein the airborne particles are selected from: bacterial, fungal, mycoplasma, and mold cells, bacterial, fungal, and mold spores, and prions.

9. The electrostatic air sampling device of claim 1, wherein the potential applied to the conical, outer electrode is less than 5,000 volts.

10. The electrostatic air sampling device of claim 1, wherein the power source additionally provides power to the collection electrode.

11. The electrostatic air sampling device of claim 10, wherein the power source is programmed to variably energize the electrode segments of the conical, outer electrode.

12. The electrostatic air sampling device of claim 1, wherein the cylindrical collection electrode is a hollow cylinder having an interior volume and further comprising:
a reservoir containing a liquid, said reservoir hydraulically connected to the collection electrode and
a pump for pumping liquid from the reservoir to the interior volume of the collection electrode such that liquid flows from the interior of the electrode and over the outer surface of the collection electrode and is returned to the reservoir.

13. The electrostatic air sampling device of claim 12, wherein the device comprises two or more electrostatic collection modules that share a common reservoir.

14. The electrostatic air sampling device of claim 12, further comprising an analyzer hydraulically connected to the reservoir, for analyzing particles collected by the sampling device.

15. The electrostatic air sampling device of claim 12, wherein the liquid is an aqueous buffer.

16. A method for collecting airborne particulates comprising:
drawing air through an electrostatic air sampling device comprising:
an electrostatic collection module comprising:
an airflow chamber comprising an air passage having an air inlet and an air outlet;
a means of drawing air into the air inlet, through the airflow chamber, and out through the air outlet;
an ionization electrode located near the air inlet, the ionization electrode being capable of ionizing airborne particles;
a conical outer electrode forming at least a part of the outer wall of the airflow chamber and having a larger diameter toward the air inlet and a smaller diameter toward the air outlet;
a cylindrical collection electrode, the exterior surface of which forms at least a part of the inner wall of the airflow chamber and upon which airborne particles deposit; and
a power source operatively connected to the electrostatic collection module, said power source providing power to energize the ionization and outer electrodes; and
recovering collected particles from the collection electrode.

17. The method according to claim 16, wherein:
the conical, outer electrode of the electrostatic collection module comprises a series of electrode segments and
the potentials applied to the electrode segments are programmed to increase the collection efficiency for desired airborne particulates.

18. The method according to claim 16, wherein: the cylindrical collection electrode is a hollow cylinder having an interior volume and the electrostatic collection module further comprises:
a reservoir containing a liquid, said reservoir hydraulically connected to the collection electrode and
a pump for pumping liquid from the reservoir to the interior volume of the collection electrode such that liquid flows from the interior of the electrode and over the outer surface of the collection electrode and is returned to the reservoir and
collected particles are recovered from the collection electrode by collecting liquid from the reservoir.

19. The method according to claim 16, wherein the airborne particles are selected from: bacterial, fungal, mycoplasma, and mold cells, bacterial, fungal, and mold spores, and prions.

20. The method according to claim 16, wherein the air inlet of the airflow chamber comprises one or more vanes that cause tangential, spiral, laminar airflow in the airflow chamber.

* * * * *